United States Patent [19]

Bowers, Jr.

[11] Patent Number: 4,514,570

[45] Date of Patent: Apr. 30, 1985

[54] PROCESS FOR THE PREPARATION OF 2,2,4-TRIMETHYL-1,2-DIHYDROQUINOLINE COMPOUNDS

[75] Inventor: Joseph S. Bowers, Jr., Kingsport, Tenn.

[73] Assignee: Eastman Kodak Company, Rochester, N.Y.

[21] Appl. No.: 585,647

[22] Filed: Mar. 2, 1984

[51] Int. Cl.$^3$ .................. C07D 215/06; C07D 215/14
[52] U.S. Cl. ..................................... 546/181; 546/178
[58] Field of Search ................................ 546/181, 178

[56] References Cited

FOREIGN PATENT DOCUMENTS 46-36625 10/1971 Japan .
9035338 8/1972 Japan .

*Primary Examiner*—Glennon H. Hollrah
*Assistant Examiner*—D. B. Springer
*Attorney, Agent, or Firm*—Clyde L. Tootle; Gary C. Bailey; J. Frederick Thomsen

[57] ABSTRACT

Disclosed is a process for preparing 2,2,4-trimethyl-1,2-dihydroquinoline compounds by reacting acetone with an aniline compound in the presence of a strongly acidic sulfonic acid-type macroreticular cation exchange resin catalyst. 2,2,4-Trimethyl-1,2-dihydroquinoline compounds are obtained in good yield and containing substantially no catalyst residue contaminant.

3 Claims, No Drawings

PROCESS FOR THE PREPARATION OF 2,2,4-TRIMETHYL-1,2-DIHYDROQUINOLINE COMPOUNDS

This invention relates to an improved process for producing hydroquinoline compounds. More particularly, it relates to a process wherein an aniline compound and acetone are condensed in the presence of a cation-exchange resin catalyst to produce 2,2,4-trimethyl-1,2-dihydroquinoline compounds.

It is known to prepare 2,2,4-trimethyl-1,2-dihydroquinoline compounds having the structure

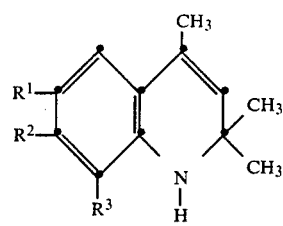

wherein $R^1$, $R^2$ and $R^3$ are various substituents by reacting the appropriate aniline compound with acetone in the presence of a catalyst.

Two processes disclosed in the prior art employ iodine and certain aromatic sulfonic acids as catalysts. Reported in Organic Synthesis, Collective Vol. III 329 is the preparation of 2,2,4-trimethyl-1,2-dihydroquinoline from aniline and acetone using iodine as a catalyst. A yield of 61–68% is reported. Disclosed in Hungarian Patent No. 157,370 (1970), abstracted at Chemical Abstracts 73:45371v, is the preparation of the same compound in a reported yield of 93% using p-toluenesulfonic acid as a catalyst.

The above processes are disadvantageous in that the hydroquinoline compounds obtained thereby are contaminated with catalyst residue which can interfere with subsequent reactions in which the hydroquinoline products are employed, e.g., in the catalytic hydrogenation of the compounds to the tetrahydro derivative the iodine or sulfur contaminant can poison common hydrogenation catalysts such as Raney nickel or platinum. Therefore, purification of the hydroquinoline compound, such as by distillation, to remove the catalyst residue is necessary. This serves to add to the production time as well as to the manufacturing cost of the product. Moreover, the overall yield is reduced due to the formation of tar during the distillation, further increasing the cost of the desired hydroquinoline product.

A method has now been found for obtaining 2,2,4-trimethyl-1,2-dihydroquinoline compounds in high yield and without the presence of unwanted catalyst residue attendant with the above prior art methods. The process of this invention allows the preparation of various hydroquinoline compounds using known reactants, i.e., acetone and certain aniline compounds. In addition, the desired dihydroquinolines are produced with a minimum of steps and at a reduced cost compared to the prior art methods since the product compound may be used without first being purified. The hydroquinoline compounds obtained by this process are known to be useful as intermediates in the preparation of other compounds useful, for example, as antioxidants, ultraviolet light stabilizers and dye couplers, as disclosed by Ger. Offen. 2,726,653 (1977); Pol. 107,925 (1980); and Japan 71 36,625 (1971).

SUMMARY OF THE INVENTION

The present invention concerns an improved process for the preparation of 2,2,4-trimethyl-1,2-dihydroquinoline compounds by reacting an aniline compound with acetone in the presence of a catalyst. The improvement comprises conducting the reaction in the presence of a catalytic amount of a strongly acidic sulfonic acid-type macroreticular cation exchange resin as the catalyst. The methyl substituted hydroquinoline compounds thus obtained may be used in further reactions without first being purified. In addition the catalyst employed in this process remains highly active after repeated use.

DETAILED DESCRIPTION OF THE INVENTION

The invention described herein relates to the preparation of 2,2,4-trimethyl-1,2-dihydroquinoline compounds. The preparation of these compounds is achieved, using an aniline compound and acetone as reactants, as in prior known methods. Unlike prior processes, however, the process of this invention is conducted in the presence of a catalytic amount of a strongly acid cation-exchange resin as catalyst. The cation-exchange resin used is a sulfonic-type strongly acid ion-exchange resin. Exemplary ion-exchange resins suitable for this process are sulfonated styrenedivinylbenzene copolymers in the H+ form. Examples of these ion-exchange resins include Amberlyst 15 ®, Amberlyst ® XN-1010, Amberlite ® IR120+, and Amberlite ® IR-118, each of which is manufactured by Rohm and Haas Company in U.S.A. (Amberlyst and Amberlite are registered trademarks of Rohm and Haas Company).

A particularly expedient catalyst for this process is Amberlyst-15 which is a macroreticular cation-exchange resin. "Amberlyst-15" is described in J.A.C.S., Vol. 84, No. 2 (1962), pages 306–306, and I & EC Product Research and Development, Vol. 1, No. 2 (1962), pages 140–144, and is a macroreticular (macroporous) sulfonic acid type cation exchange resin having pores of about 400 to 800 A., having a H+ concentration of about 4.9 milliequivalents per gram of dry resin. It can be produced by suspension polymerization of a styrene-divinyl benzene copolymer in the presence of a substance which is a good solvent for the monomers but a poor swelling agent for the polymer and sulfonating the resulting polymer by conventional means.

The catalyst may be employed in a catalytic amount, that is, any amount which exhibits a favorable comparison in the reaction as compared to the same reaction conducted in the absence of any catalyst. Preferably the catalyst will be employed in the amount of about 25 g. to about 75 g. per mole of aniline compound with about 40 g. to about 60 g. being especially preferred.

Generally, at least stoichiometric amounts of acetone and aniline compound will be employed although an excess of acetone is generally preferred, that is up to about a 4:1 mole ratio of acetone to aniline is preferred.

The temperatures at which the process of the present invention may be carried out are in the range of about 130° to 185° C. Generally, the temperature at which optimum results are achieved will vary depending on the specific catalyst employed. For Amberlyst 15, for example, the reaction will be conducted at a base pot temperature of about 150°–155° C., the maximum reaction temperature recommended by the manufacturer of the ion exchange resin.

The reaction is conducted at ambient pressure under a nitrogen purge. The reaction is conveniently carried out without the use of a solvent. However, if desired a solvent may be employed. Generally any conventional inert organic solvent may be suitably employed. Optionally, a polymerization inhibitor may also be employed in the reaction process, e.g., hydroquinone.

The 2,2,4-trimethyl-1,2-dihydroquinoline compounds which may be produced by this process are generally known in the art. These compounds may be more specifically represented by the structural formula

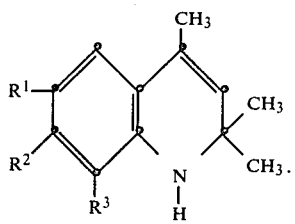
I wherein $R^1$, $R^2$, and $R^3$ may each independently be any substituent known in the art to be nonreactive under the conditions of reaction and in particular which does not undergo hydrolysis. Preferably, $R^1$, $R^2$, and $R^3$ are each independently selected from H, —$CH_3$, —$CH_2CH_3$, $OCH_3$, —$OCH_2CH_3$, Cl, and —$CH_2CH_2OH$.

. The aniline reactant is well known in the art. It may be represented by the structural formula

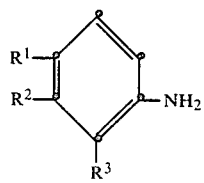
II wherein $R^1$, $R^2$, and $R^3$ are as defined above. In an especially preferred embodiment of this invention the aniline reactant is aniline or m-toluidine.

The following example is given to further illustrate the invention, but it is to be understood that the invention is not to be limited in any way by the details described therein.

EXAMPLE 1

To a 1.0 l flask was added 100 g Amberlyst 15 ion exchange resin (dry), 50 ml acetone and 54 g m-toluidine. The slurry was stirred for 1 hour.

Charged to the catalyst slurry prepared above was 214 g m-toluidine and 0.1 g hydroquinone. The reaction mixture was heated slowly to 150°–155° C. distilling off the acetone in the process. 1000 ml acetone was added at such a rate that the pot temperature remained at 150°–155° C. and the still head take-off temperature remained at 55°–65° C. The reaction was discontinued after the content of m-toluidine was below 5.0% but above 1.0% (continuing the reaction to below 1.0% content of m-toluidine results in a decrease in overall product yield). Reaction time was approximately 48 hours. The product solution was separated from the catalyst and the acetone was stripped under vacuum. Total yield obtained of 2,2,4,7-tetramethyl-1,2-dihydroquinoline was 344 g (92%).

The invention has been described in detail with particular reference to preferred embodiments thereof, but it will be understood that variations and modifications can be effected within the spirit and scope of the invention.

I claim:

1. In a process of producing 2,2,4-trimethyl-1,2-dihydroquinoline compounds by reacting an aniline compound with acetone in the presence of a catalyst, the improvement which comprises carrying out said reaction in the presence of a strongly acidic sulfonic acid-type macroreticular cation exchange resin as the catalyst.

2. The process of claim 1 wherein said aniline compound is aniline or meta-toluidine.

3. In a process for preparing a compound having the structural formula

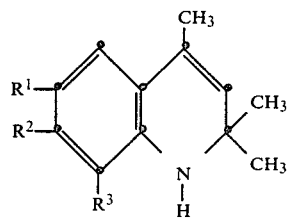

by reacting acetone with an aniline compound having the structural formula

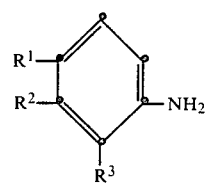

wherein $R^1$, $R^2$, and $R^3$ are independently selected from H, —$CH_3$, —$CH_2CH_3$, —$OCH_3$, —$OCH_2CH_3$, —Cl, and —$CH_2CH_2OH$, wherein the reaction is carried out in the presence of a catalyst, the improvement which comprises carrying out said reaction in the presence of a strongly acidic sulfonic acid-type macroreticular cation exchange resin as catalyst.

* * * * *